US011360037B1

(12) United States Patent
Wu et al.

(10) Patent No.: US 11,360,037 B1
(45) Date of Patent: Jun. 14, 2022

(54) CLASSIFIED CHARACTERIZATION METHOD FOR CONNECTIVITY OF ORGANIC MATTER (OM)-HOSTED PORES IN SHALE

(71) Applicant: INSTITUTE OF GEOLOGY AND GEOPHYSICS, CHINESE ACADEMY OF SCIENCES, Beijing (CN)

(72) Inventors: Jianguo Wu, Beijing (CN); Jijin Yang, Beijing (CN); Guoliang Li, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/581,927

(22) Filed: Jan. 23, 2022

(30) Foreign Application Priority Data

Oct. 28, 2021 (CN) .......................... 202111264247.0

(51) Int. Cl.
*G01N 23/2251* (2018.01)
*G01N 33/24* (2006.01)
(Continued)

(52) U.S. Cl.
CPC .......... *G01N 23/2251* (2013.01); *G01N 1/32* (2013.01); *G01N 33/24* (2013.01); *G06T 7/11* (2017.01);
(Continued)

(58) Field of Classification Search
None
See application file for complete search history.

(56) References Cited

U.S. PATENT DOCUMENTS 8,756,042 B2 * 6/2014 Tan .......................... G01V 1/28
703/2
8,908,925 B2 * 12/2014 Hurley .................... E21B 49/00
382/109
(Continued)

FOREIGN PATENT DOCUMENTS

AU 2020102843 A4 * 12/2020
CN 109187305 A 1/2019
(Continued)

OTHER PUBLICATIONS

Nyujia Peng, Pore structure and fractal characteristics of Wufeng and lower member of Longmaxi shales in western Hubei and eastern Chongqing regions, China University of Geosciences, 2019, pp. 1-190, China Academic Journal Electronic Publishing House.

*Primary Examiner* — Mia M Thomas
(74) *Attorney, Agent, or Firm* — Bayramoglu Law Offices LLC (57) ABSTRACT

A classified characterization method for connectivity of organic matter (OM)-hosted pores in shale includes: scanning a shale sample according to a preset imaging area through a scanning electron microscope to acquire a 2D image of the shale sample; extracting pore parameters of each OM in the 2D image by Avizo software; acquiring a class number of OM sets according to the pore parameters; performing 3D reconstruction on each class of OM sets through a focused ion beam-helium ion microscope to acquire reconstructed 3D models of the OM; acquiring a pore connectivity parameter by the Avizo software; and acquiring an evaluation index for overall connectivity of the OM-hosted pores in the shale based on the pore connectivity parameter. The classified characterization method is based on the morphologically quantitative classification of the
(Continued)

OM-hosted pores, and can realize the 3D characterization of connectivity of pores below 10 nm.

8 Claims, 4 Drawing Sheets

(51) Int. Cl.
| | |
|---|---|
| *G06V 10/764* | (2022.01) |
| *G06V 10/762* | (2022.01) |
| *G06T 17/00* | (2006.01) |
| *G06T 7/136* | (2017.01) |
| *G06T 7/11* | (2017.01) |
| *G06T 7/60* | (2017.01) |
| *G01N 1/32* | (2006.01) |

(52) U.S. Cl.
CPC ............ *G06T 7/136* (2017.01); *G06T 7/60* (2013.01); *G06T 17/00* (2013.01); *G06V 10/763* (2022.01); *G06V 10/764* (2022.01); *G01N 2223/07* (2013.01); *G01N 2223/401* (2013.01); *G01N 2223/418* (2013.01); *G01N 2223/507* (2013.01); *G01N 2223/616* (2013.01); *G06T 2207/10061* (2013.01)

(56) References Cited

U.S. PATENT DOCUMENTS

| | | | |
|---|---|---|---|
| 8,909,508 B2* | 12/2014 | Hurley | G06T 7/136 703/10 |
| 11,231,349 B1* | 1/2022 | Du | G01N 1/32 |
| 2011/0004447 A1* | 1/2011 | Hurley | G06T 17/00 702/179 |
| 2012/0239361 A1* | 9/2012 | Vargas-Guzman | G01V 99/005 703/6 |
| 2013/0301794 A1* | 11/2013 | Grader | G01N 23/087 378/5 |
| 2014/0319339 A1* | 10/2014 | Hall | B81C 1/00087 435/5 |
| 2016/0195637 A1* | 7/2016 | Honarpour | G01V 5/12 378/4 |
| 2018/0003653 A1 | 1/2018 | Tinni et al. | |
| 2019/0154597 A1* | 5/2019 | Zhang | G01N 23/046 |
| 2020/0149394 A1* | 5/2020 | Hao | G01N 33/241 |
| 2020/0254432 A1* | 8/2020 | Shirman | B01J 35/0013 |

FOREIGN PATENT DOCUMENTS

| | | |
|---|---|---|
| CN | 110210460 A | 9/2019 |
| CN | 113158490 A | 7/2021 |
| CN | 113176187 A | 7/2021 |

\* cited by examiner

CLASSIFIED CHARACTERIZATION METHOD FOR CONNECTIVITY OF ORGANIC MATTER (OM)-HOSTED PORES IN SHALE

CROSS REFERENCE TO THE RELATED APPLICATIONS

This application is based upon and claims priority to Chinese Patent Application No. 202111264247.0, filed on Oct. 28, 2021, the entire contents of which are incorporated herein by reference.

TECHNICAL FIELD

The present invention belongs to the technical field of oil and gas exploration, and more particularly, relates to a classified characterization method for connectivity of organic matter (OM)-hosted pores in shale.

BACKGROUND

OM-hosted pores are the main matrix pores in shale, and their connectivity fundamentally affects the desorption-diffusion flow of shale gas. Therefore, the quantitative characterization of connectivity of OM-hosted pores is of great significance for evaluating shale gas development potential, optimizing shale gas development plans and improving shale gas recovery.

At present, the characterization of the connectivity mainly adopts mercury intrusion porosimetry, nano-computed tomography (CT) and focused ion beam-scanning electron microscopy (FIB-SEM). In mercury intrusion porosimetry, the fluid properties of the mercury used are too different from the gas properties, the interaction between the fluid and the surface varies, and the high pressure may destroy the shale pore structure. Therefore, whether the connectivity measured by mercury intrusion porosimetry is applicable to shale gas flow is highly questionable. Nano-CT and FIB-SEM are not affected by the interaction between the fluid and the surface as well as the occlusion effect, and they can reconstruct the three-dimensional (3D) image of the pores to display the connectivity of the pores. They can be combined with digital core technology to further quantitatively analyze the rich information of nano-pores, such as the porosity, pore size distribution, pore volume, specific surface area, throat-to-pore coordination number and tortuosity. However, scholars pointed out that since the precision of nano-CT is generally above 50 nm and the precision of FIB-SEM is above 10 nm, they can hardly reconstruct pores below 10 nm. The pore size distribution shows that there are a large number of OM-hosted pores below 10 nm, which can serve as throats to connect relatively large pores. If the small pores are not reconstructed accurately, a major misjudgment will be resulted in connectivity evaluation. Focused ion beam-helium ion microscopy (FIB-HIM) is an emerging 3D reconstruction technology with a resolution up to 0.5 nm, which can effectively solve the 3D reconstruction problem of OM-hosted pores below 10 nm.

The regions reconstructed by nano-CT, FIB-SEM and FIB-HIM are generally in the micrometer scale. How such a small volume can represent the connectivity of OM-hosted pores in bulk shale has always been a difficult problem for scholars. Preliminary research shows that the development of OM-hosted pores is morphologically heterogeneous, and there are obvious differences in pore size, pore density, pore shape and pore distribution. These morphological differences reflect the connectivity differences of pores in the 3D space. Therefore, based on the idea of clustering analysis, the morphological characteristics of OM-hosted pores can be quantitatively classified, and then the connectivity of each class of OM-hosted pores can be quantitatively characterized. This design can greatly reduce the workload of characterization and make the characterization results more representative. The current research on the morphological differences of OM-hosted pores is mostly limited to qualitative image description, and there is no solution for quantitative differentiation based on parameters such as density, size, sorting and shape. This is unfavorable for fully understanding the development characteristics of OM-hosted pores and quantitatively characterizing the connectivity of OM-hosted pores.

SUMMARY

In order to solve the above problems in the prior art, that is, in order to study the development characteristics of OM-hosted pores in order to acquire reliable information for characterizing connectivity of the OM-hosted pores, the present invention provides a classified characterization method for the connectivity of OM-hosted pores in shale. The method includes the following steps: S100: scanning a shale sample according to a preset imaging area through a scanning electron microscope to acquire a two-dimensional (2D) image of the shale sample;

S200: extracting pore parameters of each OM in the 2D image by Avizo software, the pore parameters including porosity, median pore radius, pore sorting coefficient, and pore shape factor of the OM;

S300: acquiring a class number of OM sets according to the pore parameters;

S400: performing 3D reconstruction on each class of OM sets through a focused ion beam-helium ion microscope to acquire reconstructed 3D models of the OM;

S500: acquiring a pore connectivity parameter based on the reconstructed 3D models of the OM by the Avizo software; and S600: acquiring an evaluation index for overall connectivity of the OM-hosted pores in the shale based on the pore connectivity parameter.

In some preferred examples, a method for acquiring the 2D image may include: S110: performing argon ion polishing on the shale sample to acquire a pretreated shale sample;

S120: setting an acceleration voltage of the scanning electron microscope to 1.2 kV, and acquiring a secondary electron signal on a surface of the pretreated shale sample at a preset imaging resolution; and S130: performing, by the scanning electron microscope, continuous 2D splicing imaging on the pretreated shale sample according to the preset imaging area, where the preset imaging area is S, and S>100 μm*100 μm.

In some preferred examples, the preset imaging resolution may be 4 nm/pixel; and the preset imaging area may be 260 μm*260 μm.

In some preferred examples, a method for extracting the pore parameters may include: S210: preprocessing the 2D image to acquire a preprocessed image, where the preprocessing includes gray scale correction and filtering;

S220: extracting all OM in the preprocessed image by threshold segmentation based on a grayscale difference, and storing in a binarized form to acquire a binarized image;

S230: acquiring a first OM region image based on the binarized image, where the first OM region image includes N first OM regions, and each of the N first OM regions has a closed-loop structure composed of the same grayscale;

S240: assimilating different grayscales in the N first OM regions through a filling command to acquire a filled second OM region image, where the second OM region image includes N second OM regions, and the N second OM regions correspond to the N first OM regions, respectively;

S250: sequentially assigning values to the N second OM regions through MATLAB software to acquire a third OM region image with different assigned regions, where the third OM region image includes N third OM regions, and assignment numbers of the N third OM regions are defined by a first set of Arabic numerals in a first order;

S260: sequentially assigning values to the N first OM regions through the MATLAB software to acquire a fourth OM region image with different assigned regions, where the fourth OM region image includes N fourth OM regions, and assignment numbers of the N fourth OM regions are defined by a second set of Arabic numerals in a second order; and the second order is set in accordance with the first order, and the first set of Arabic numerals is set in accordance with the second set of Arabic numerals;

S270: subtracting the third OM region image from the fourth OM region image to acquire a fifth OM region image, where the fifth OM region image includes N fifth OM regions, and the N fifth OM regions are labeled pore images to which values are assigned sequentially; and S280: acquiring the porosity $\varphi_{om}$, the median pore radius Md, the pore sorting coefficient $S_o$ and the pore shape factor SF based on the fifth OM region image;

$\varphi_{OM}=A_p/(A_{OM}+A_p)*100\%$, where $A_{OM}$ is an area of a single OM, and $A_P$ is an area of pores in the single OM;

the median pore radius Md is a pore radius corresponding to 50% on a cumulative pore size distribution curve, where the cumulative pore size distribution curve is a distribution curve of a pore radius and a cumulative percentage of the pore area; and $S_o=P_{25}/P_{75}$ where, $P_{25}$ and $P_{75}$ respectively represent pore radii corresponding to cumulative percentages 25% and 75% of the pore area on the cumulative pore size distribution curve;

calculating N pore shape factors $SF_i$ corresponding to the N fifth OM regions, $SF_i=4\pi A_{pi}/L_{pi}^2$, where $SF_i$ is a pore shape factor of an i-th pore, $A_{pi}$ is an area of the i-th pore, and $L_{pi}$ is a perimeter of the i-th pore, i∈[1, N];

selecting pore shape factors with the same value to form a set of identical factors, where the N pore shape factors form M sets of identical factors, and M∈(1, N);

where, each of the sets of identical factors includes n pore shape factors, n∈(1, N);

acquiring a sum of areas of pores corresponding to each set of identical factors to form a set of pore areas, where the M sets of identical factors form M sets of pore areas; and acquiring, based on the M sets of pore areas, a pore shape factor corresponding to a set of pore areas with a maximum sum of areas to be the pore shape factor SF.

In some preferred examples, the class numbers of the OM sets may be acquired as follows: S310: performing an initial classification on the OM sets through a K means clustering algorithm based on the porosity $\varphi_{OM}$, the median pore radius Md, the pore sorting coefficient $S_o$ and the pore shape factor SF, where an initial class number of the OM sets is K, K≥2, and each of the OM sets includes N OM;

S320: calculating a coefficient of variation $CV_j$ of each class of OM set through the K-means clustering algorithm, $CV_j=\sigma_j/\mu_j$, where j is $\varphi_{OM}$, Md, $S_o$ or SF;

S330: if any coefficient of variation $CV_j$ in the K classes of OM sets satisfies $CV_j \leq 0.5$, taking the initial class number K of the OM sets as the class number of the OM sets; and otherwise, proceeding to S340; and S340: setting the initial class number of the OM sets to K=K+1, and repeating S320 to S330.

In some preferred examples, $$\sigma_{\varphi_{OM}} = \sqrt{\frac{\sum_{i=1}^{N}(\varphi_{OM,i}-\mu_{\varphi_{OM}})^2}{N}},$$

where $\mu_{\varphi OM}$ is a standard deviation (SD) of a porosities corresponding to the N OM in each class of OM set;

$$\mu_{\varphi_{OM}} = \frac{\sum_{i=1}^{N}\varphi_{OM,i}}{N},$$

where $\mu_{\varphi OM}$ is a mean of the porosities corresponding to the N OM in each class of OM set;

$$\sigma_{Md} = \sqrt{\frac{\sum_{i=1}^{N}(Md_i-\mu_{Md})^2}{N}},$$

where $\sigma_{MD}$ is an SD of median pore radii corresponding to the N OM in each class of OM set;

$$\mu_{Md} = \frac{\sum_{i=1}^{N}Md_i}{N},$$

where $\mu_{Md}$ is a mean of the median pore radii corresponding to the N OM in each class of OM set:

$$\sigma_{S_o} = \sqrt{\frac{\sum_{i=1}^{N}(S_{o,i}-\mu_{S_o})^2}{N}},$$

where $\sigma_{S_o}$ is an SD of pore sorting coefficients corresponding to the N OM in each class of OM set;

$$\mu_{S_o} = \frac{\sum_{i=1}^{N}S_{o,i}}{N},$$

where $\mu_{S_o}$ is a mean of the pore sorting coefficients corresponding to the N OM in each class of OM set;

$$\sigma_{SF} = \sqrt{\frac{\sum_{i=1}^{N}(SF_i-\mu_{SF})^2}{N}},$$

where $\sigma_{SF}$ is an SD of pore shape factors corresponding to the N OM in each class of OM set; and $$\mu_{SF} = \frac{\sum_{i=1}^{N} SF_i}{N},$$

where $\mu_{SF}$ is a mean of the pore shape factors corresponding to the N OM in each class of OM set.

In some preferred examples, a method for acquiring the reconstructed 3D models of the OM may include: screening the K classes of OM sets based on a preset area threshold by the focused ion beam-helium ion microscope to acquire the reconstructed 3D models of the OM, where the preset area threshold is S1, S1>5 μm*5 μm.

In some preferred examples, the pore connectivity parameter may be $P_m$, $P_m = V_{Cm}/V_{Tm}$, where $P_m$ is a pore connectivity parameter of an m-th class of OM set, $V_{Cm}$ is a volume of connected pores in the m-th class of OM set, and $V_{Tm}$ is a volume of total pores in the m-th class of OM set; m∈[1, K], where K is the class number of the OM sets.

In some preferred examples, the evaluation index for the overall connectivity may be $$C_r, C_r = \frac{\left\{\sum_{m}^{k}(P_m * \emptyset_m)\right\}}{\emptyset_{total}} * 100\%,$$

where $\emptyset_m$ is a total plane porosity of the m-th class of OM set; $\emptyset_{total}$ and is a total plane porosity of the K classes of OM sets in the shale sample;

$\lfloor_m = \Sigma\emptyset_o$, where $\emptyset_o$ is a plane porosity of an o-th OM in each class of OM set, o∈[1, N];

$\emptyset_o = S_{po}/S*100\%$;

$S_{po} = \Sigma A_{pi}$, where $S_{po}$ is an area of all pores in the o-th OM in each class of OM set;

$\emptyset_{total} = \Sigma\emptyset_m$;

In some preferred examples, SF∈(0, 1].

The present invention has the following beneficial effects. 1) The current research on the morphological differences of OM-hosted pores is mostly limited to qualitative image description, and there is no solution for quantitative differentiation based on parameters such as density, size, sorting and shape. The method of the present invention can fully understand the development characteristics of OM-hosted pores and quantitatively characterize the connectivity of OM-hosted pores.

2) The method of the present invention is based on the morphologically quantitative classification of OM-hosted pores, and can realize the 3D characterization of connectivity of pores below 10 nm, solving the problem of unrepresentative characterization of the existing methods.

BRIEF DESCRIPTION OF THE DRAWINGS

Other features, objectives and advantages of this application will become more apparent upon reading the detailed description of the non-restrictive examples with reference to the following accompanying drawings.

DETAILED DESCRIPTION OF THE EMBODIMENTS

The preferred implementations of the present invention are described below with reference to the accompanying drawings. Those skilled in the art should understand that the implementations herein are merely intended to explain the technical principles of the present invention, rather than to limit the protection scope of the present invention.

The present invention provides a classified characterization method for connectivity of OM-hosted pores in shale. The method includes the following steps: S100: scan a shale sample according to a preset imaging area through a scanning electron microscope to acquire a 2D image of the shale sample; S200: extract pore parameters of each OM in the 2D image by Avizo software, the pore parameters including porosity, median pore radius, pore sorting coefficient, and pore shape factor of the OM; S300: acquire a class number of OM sets according to the pore parameters; S400: perform 3D reconstruction on each class of OM sets through a focused ion beam-helium ion microscope to acquire reconstructed 3D models of the OM; S500: acquire a pore connectivity parameter based on the reconstructed 3D models of the OM by the Avizo software; and S600: acquire an evaluation index for overall connectivity of the OM-hosted pores in the shale based on the pore connectivity parameter.

The present invention is further described below with reference to the drawings and examples.

Figure 1:
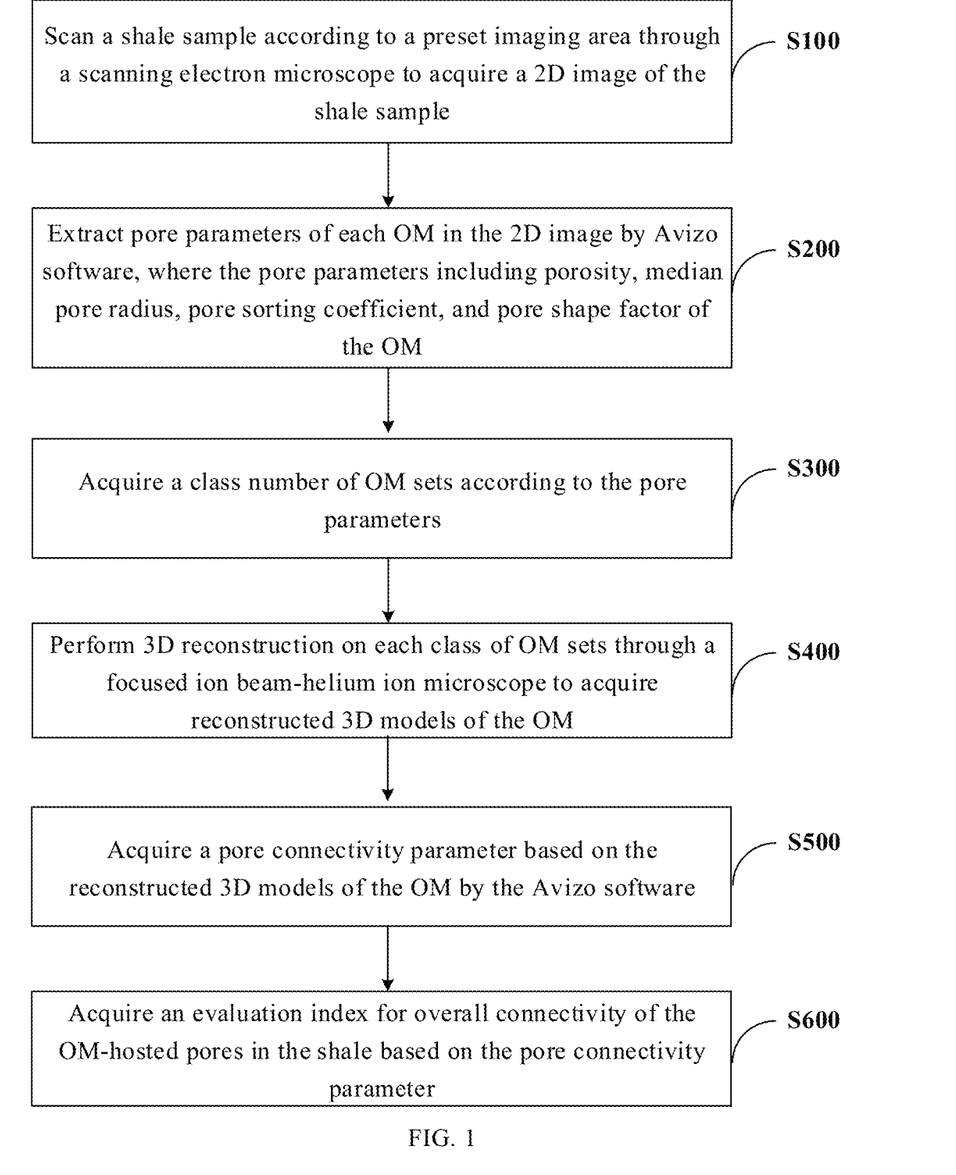
FIG. 1 is a flowchart of a specific example of the present invention.
Figure 2:
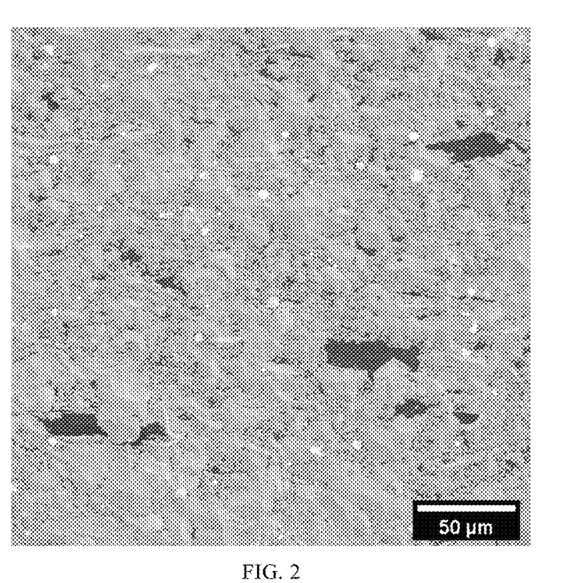
FIG. 2 is a 2D SEM image of a specific example of the present invention.

The present invention provides a classified characterization method for connectivity of OM-hosted pores in shale. As shown in FIGS. 1 and 2, the method includes the following steps. S100: Scan a shale sample according to a preset imaging area through a scanning electron microscope to acquire a 2D image of the shale sample.

Specifically, a method for acquiring the 2D image includes: S110: perform argon ion polishing on the shale sample to acquire a pretreated shale sample; S120: set an acceleration voltage of the scanning electron microscope to 1.2 kV, and acquire a secondary electron signal on a surface of the pretreated shale sample at a preset imaging resolution; and S130: perform, by the scanning electron microscope, continuous 2D splicing imaging on the pretreated shale sample according to the preset imaging area to acquire an image shown in FIG. 2.

In this example, the preset imaging area is S, S>100 μm*100 μm, which ensures that the scanning result meets the test requirement.

Further, the preset imaging resolution is above 10 nm/pixel, which ensures that the scanning result of the shale sample is consistent with one expected.

Preferably, the preset imaging resolution is 4 nm/pixel.

Preferably, the preset imaging area is 260 μm*260 μm.

S200: Extract pore parameters of each OM in the 2D image by Avizo software, the pore parameters including porosity, median pore radius, pore sorting coefficient, and pore shape factor of the OM.

Specifically, a method for extracting the pore parameters includes the following. S210: Preprocess the 2D image to acquire a preprocessed image, where the preprocessing includes grayscale correction and filtering. The grayscale image acquired by SEM scanning has different degrees of noise. The filtering is a process of denoising the grayscale image to further acquire an accurate image through grayscale correction and filtering. Common image filtering methods include mean filtering, median filtering, Gaussian filtering, etc. Preferably, in this example, a non-local means method is used to filter the acquired 2D image.

Figure 3:
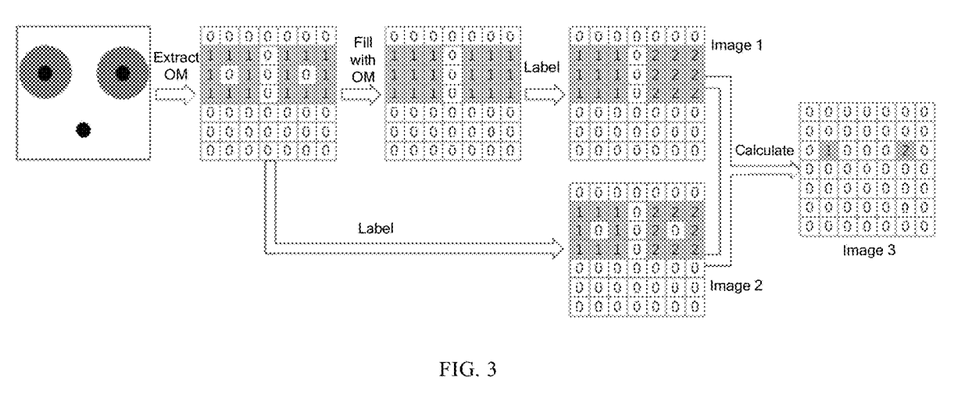
FIG. 3 is a schematic view of differentiating OM-hosted pores according to a specific example of the present invention.

S220: Extract the OM. Specifically, this step includes the following: extract all OM in the preprocessed image by threshold segmentation based on a grayscale difference, and store in a binarized form to acquire a binarized image. Referring to FIG. 3, in this example, in the filtered image, OM is shown in gray, pores are shown in black, and inorganic minerals are shown in white. Different substances have different grayscales in the grayscale image, and the threshold segmentation is a method of segmenting substances according to a grayscale range. In this example, the grayscale of the OM is 70-145. By setting the grayscale threshold of the OM, all OM can be extracted, and the extraction result is stored in the form of binary image.

S230: Acquire a first OM region image based on the binarized image, where the first OM region image includes N first OM regions, and each of the N first OM regions has a closed-loop structure composed of the same grayscale. In this example, 0 represents background and 1 represents OM.

S240: Fill with OM. Specifically, this step includes the following: assimilate different grayscales in the N first OM regions through a filling command to acquire a filled second OM region image, where the second OM region image includes N second OM regions, and the N second OM regions correspond to the N first OM regions, respectively. Assimilation is to fill different grayscales inside the OM with a closed-loop structure or a closed-loop shape to the same grayscale as the OM. In this example, the assimilation is to fill the value inside the OM with a closed-loop structure or a closed-loop shape with 1.

S250: Perform labeling processing on each filled second OM region. Specifically, this step includes the following: sequentially assign values to the N second OM regions through MATLAB software to acquire a third OM region image (denoted as an image 1 in this example) with different assigned regions, where the third OM region image includes N third OM regions, and assignment numbers of the N third OM regions are defined by a first set of Arabic numerals in a first order.

S260: Sequentially assign values to the N first OM regions through the MATLAB software to acquire a fourth OM region image (denoted as an image 2 in this example) with different assigned regions, where the fourth OM region image includes N fourth OM regions, and assignment numbers of the N fourth OM regions are defined by a second set of Arabic numerals in a second order; and the second order is set in accordance with the first order, and the first set of Arabic numerals is set in accordance with the second set of Arabic numerals.

S270: Image calculation. Specifically, this step includes the following: subtract the third OM region image from the fourth OM region image to acquire a fifth OM region image (denoted as an image 3 in this example), where the fifth OM region image includes N fifth OM regions, and the N fifth OM regions are labeled pore images to which values are assigned sequentially. In the image 3, the pores within the same OM have the same grayscale, and the pores within different OM have different grayscales, based on which the source of the pores can be determined. It should be noted that in this pore image, there is only one pore labeled 1, and only one pore labeled 2. The number of labels in this example does not limit the protection scope of the present invention, and this example is merely one of the examples of the present invention.

S280: Acquire the porosity $\varphi_{OM}$, the median pore radius Md, the pore sorting coefficient $S_o$ and the pore shape factor SF based on the fifth OM region image.

The porosity of each OM is $\varphi_{OM}=A_p/(A_{OM}+A_p)*100\%$, where $A_{OM}$ is an area of a single OM, and $A_p$ is an area of pores in the single OM.

The median pore radius Md is a pore radius corresponding to 50% on a cumulative pore size distribution curve, where the cumulative pore size distribution curve is a distribution curve of a pore radius and a cumulative percentage of the pore area. The area $A_{OM}$ of each OM in the image 2 and the area $A_{Pi}$, perimeter $L_{pi}$ and radius $r_i$ of each pore in the image 3 are acquired by the Avizo software. In each OM, when the radius is a, the corresponding cumulative percentage of the pore area is b, $$b = \frac{\sum_{a}^{r_{max}} A_{pa}}{A_p} * 100\%;$$

where $r_{max}$ represents a maximum pore radius in a single OM, $A_{Pa}$ represents an area corresponding to a pore with a radius of a, and $A_P$ represents a total area of all pores in the corresponding single OM. In the cumulative pore size distribution curve, the reverse order of the pore radius (the value on the left is greater than that on the right) represents the abscissa, and the cumulative percentage of pore area represents the ordinate. The point (a,b) on the curve represents that the total percentage of the pore area is b when the radius is not less than a.

The pore sorting coefficient is $S_o=P_{25}/P_{75}$, where, $P_{25}$ and $P_{75}$ respectively represent pore radii corresponding to cumulative percentages 25% and 75% of the pore area on the cumulative pore size distribution curve.

In this example, when $S_o\in[1,2.5]$, it indicates a high pore uniformity. When $S_o\in[2.5,4.0]$, it indicates a moderate pore uniformity. When $S_o>4.0$, it indicates a low pore uniformity.

The pore shape factor SF is determined as follows. First, calculate N pore shape factors $SF_i$ corresponding to the N fifth OM regions, $SF_i=4\pi A_{pi}/L_{pi}^2$, where $SF_i$ is a pore shape factor of an i-th pore, $A_{pi}$ is an area of the i-th pore, and $L_{pi}$ is a perimeter of the i-th pore, $i\in[1, N]$.

Second, select pore shape factors with the same value to form a set of identical factors, where the N pore shape factors form M sets of identical factors, and $M\in(1, N)$.

Each of the sets of identical factors includes n pore shape factors, $n\in(1, N)$.

Third, acquire a sum of areas of pores corresponding to each set of identical factors to form a set of pore areas, where the M sets of identical factors form M sets of pore areas.

Fourth, acquire, based on the M sets of pore areas, a pore shape factor corresponding to a set of pore areas with a maximum sum of areas to be the pore shape factor SF.

In this example, SF∈(0, 1]. Further, SF is a decimal between 0 and 1 (including 1).

S300: Acquire a class number of OM sets according to the pore parameters, where each of the OM sets includes N OM.

Figure 4:
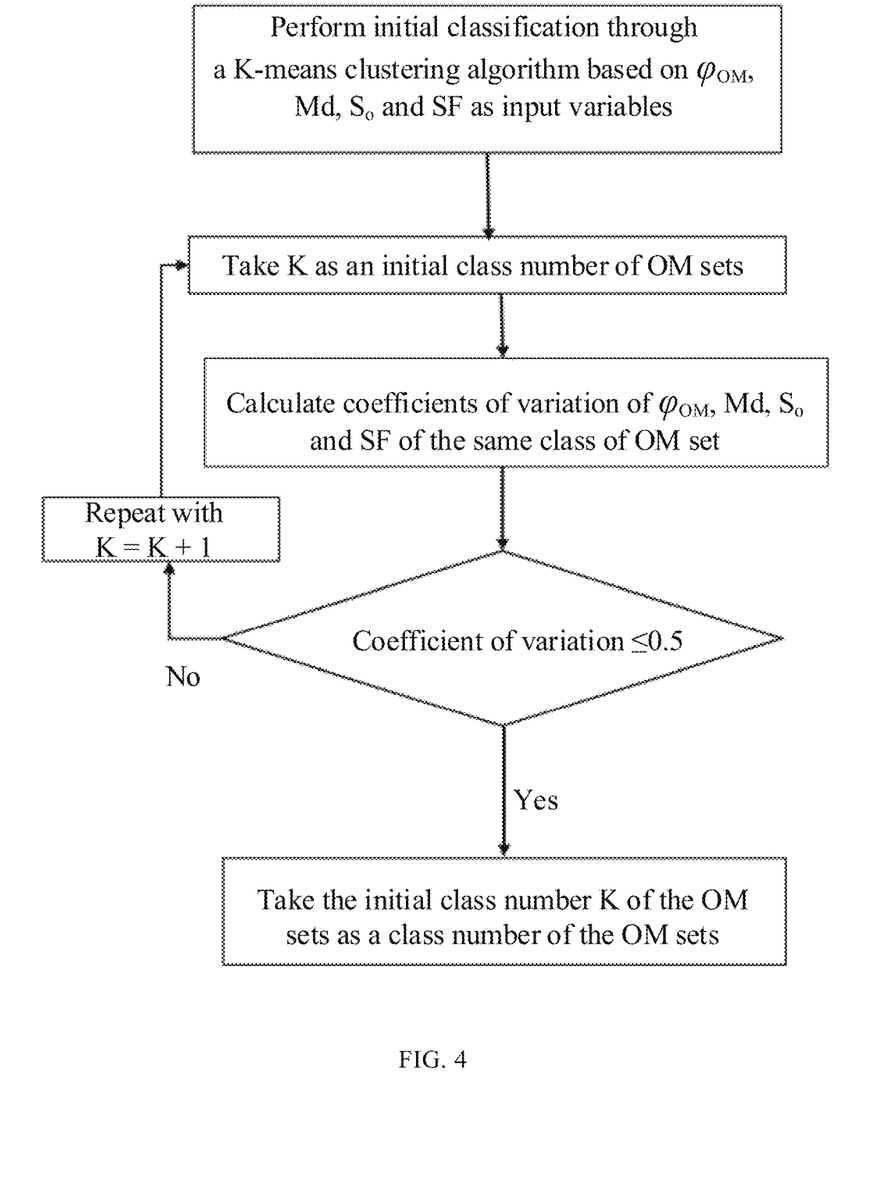
FIG. 4 is a flowchart of classifying OM sets according to a specific example of the present invention.
Figure 5:
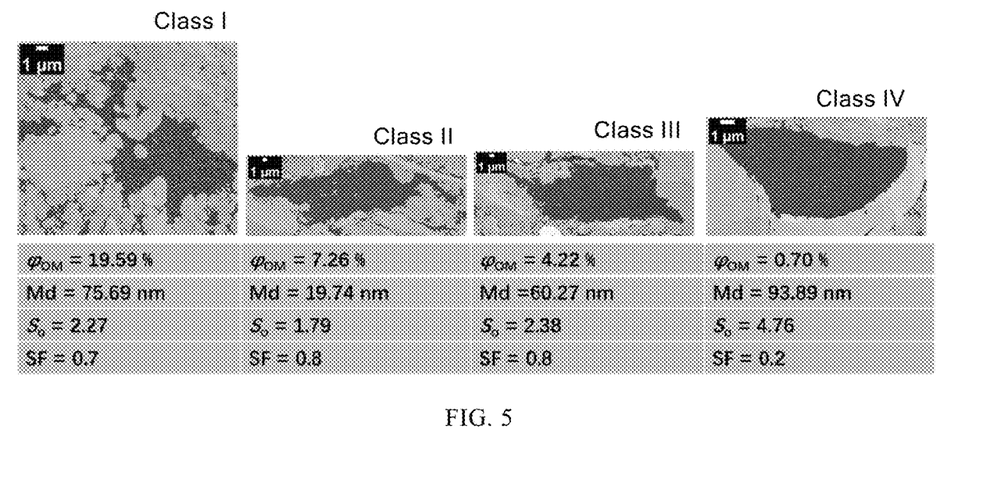
FIG. 5 is a flowchart of representative OM images and pore parameters according to a specific example of the present invention.

Referring to FIGS. 4 and 5, specifically, the class numbers of the OM sets are acquired as follows. S310: Perform an initial classification on the OM sets through a K means clustering algorithm based on the porosity $\varphi_{OM}$, the median pore radius Md, the pore sorting coefficient $S_o$ and the pore shape factor SF, where an initial class number of the OM sets is K, K≥2.

S320: Calculate a coefficient of variation $CV_j$ of each class of OM set through the K-means clustering algorithm, $CV_j = \sigma_j / \mu_j$, where j is $\varphi_{OM}$, Md, $S_o$ or SF.

S330: If any coefficient of variation $CV_j$ in the K classes of OM sets satisfies $CV_j \leq 0.5$, take the initial class number K OM sets as class number of the OM sets; and otherwise, proceed to S340.

S340: Set the initial class number of the OM sets to K=K+1, and repeating S320 to S330.

$$\sigma_{\varphi OM} = \sqrt{\frac{\sum_{i=1}^{N}(\varphi_{OM,i} - \mu_{\varphi OM})^2}{N}},$$

where $\sigma_{\varphi OM}$ is an SD of a porosities corresponding to the N OM in each class of OM set; and $$\mu_{\varphi OM} = \frac{\sum_{i=1}^{N}\varphi_{OM,i}}{N},$$

where $\mu_{\varphi OM}$ is a mean of the porosities corresponding to the N OM in each class of OM set;

$$\sigma_{Md} = \sqrt{\frac{\sum_{i=1}^{N}(Md_i - \mu_{Md})^2}{N}},$$

where $\sigma_{Md}$ is an SD of median pore radii corresponding to the N OM in each class of OM set;

$$\mu_{Md} = \frac{\sum_{i=1}^{N}Md_i}{N},$$

where $\mu_{Md}$ is a mean of the median pore radii corresponding to the N OM in each class of OM set;

$$\sigma_{S_o} = \sqrt{\frac{\sum_{i=1}^{N}(S_{o,i} - \mu_{S_o})^2}{N}},$$

where $\sigma_{S_o}$ is an SD of pore sorting coefficients corresponding to the N OM in each class of OM set;

$$\mu_{S_o} = \frac{\sum_{i=1}^{N}S_{o,i}}{N},$$

where $\mu_{S_o}$ is a mean of the pore sorting coefficients corresponding to the N OM in each class of OM set;

$$\sigma_{SF} = \sqrt{\frac{\sum_{i=1}^{N}(SF_i - \mu_{SF})^2}{N}},$$

where $\sigma_{SF}$ is an SD of pore shape factors corresponding to the N OM in each class of OM set; and $$\mu_{SF} = \frac{\sum_{i=1}^{N}SF_i}{N},$$

where $\mu_{SF}$ is a mean of the pore shape factors corresponding to the N OM in each class of OM set.

In this example, the K-means algorithm is used to divide a given sample set into K classes according to the sample distance. K is a specified value, the optimal value of which is determined by continuously increasing. The initial K is set to 2, that is, all OM sets are initially divided into two classes, and an iterative cycle is performed. FIG. 5 shows representative OM images and pore parameters. When K is 4, the criterion of coefficient of variation is satisfied, and the classification ends. Therefore, the OM sets are finally divided into four classes.

S400: Perform 3D reconstruction on each class of OM sets through a focused ion beam-helium ion microscope to acquire reconstructed 3D models of the OM. FIB-HIM maintains consistent 3D reconstruction parameters for each class of OM set. The final 3D reconstruction volume of FIB-HIM maintains consistent, and the voxels of the 3D models reconstructed by FIB-HIM at least reach 3 nm*3 nm*3 nm.

Further, a method for acquiring the reconstructed 3D models of the OM includes: screen the K classes of OM sets based on a preset area threshold by the focused ion beam-helium ion microscope to acquire the reconstructed 3D models of the OM, where the preset area threshold is S1, S1>5 μm*5 μm.

Figure 6:
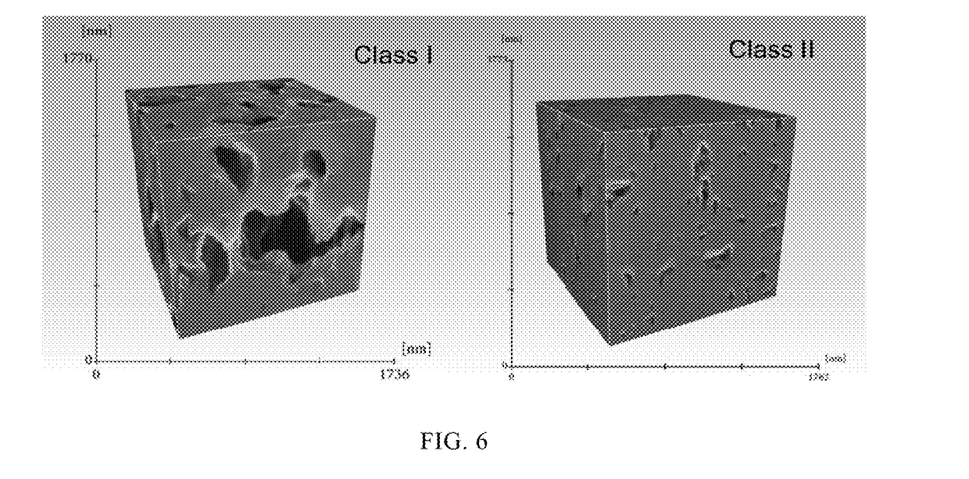
FIG. 6 shows 3D models of OM of class I and class II OM sets, reconstructed by using an FIB-HIM, according to a specific example of the present invention.

Referring to FIGS. 5 and 6, representatives are selected from the four classes of OM sets respectively, and a basic requirement is that the horizontal and vertical dimensions of the OM sets are greater than 5 μm*5 μm. The images and pore parameters of the selected four representative classes of OM sets are shown in FIG. 5.

Specifically, in the process of operating the FIB-HIM, one acceptable OM is selected from each class of OM set based on a preset area threshold, that is, K acceptable OM is selected from the K classes of OM sets. Then the 3D reconstruction of the K OM is carried out. Specifically, a sample stage is moved to place the HIM to an OM region to be tested. The sample stage is rotated and tilted to 54°. The position of the sample stage is adjusted such that the scan areas of the HIM and the FIB are on the OM to be tested. The following parameters are set: HIM accelerating voltage 30 kV, beam current 0.5 pA, imaging resolution 1 nm/pixel, imaging area 1.5 μm*1.5 μm; FIB slice thickness 3 nm/slice, and total thickness 1.5 μm. A program is started to acquire a 3D model of the OM. In this example, the 3D FIB-HIM models of the class I and class II OM of the four classes of OM are shown in FIG. 6.

S500: Acquire a pore connectivity parameter based on the reconstructed 3D models of the OM by the Avizo software, where the pore connectivity parameter is $P_m$, $P_m = V_{Cm}/V_{Tm}$, where $P_m$ is a pore connectivity parameter of an m-th class of OM set, $V_{Cm}$ is a volume of connected pores in the m-th class of OM set, and $V_{Tm}$ is a volume of total pores in the m-th class of OM set; m∈[1, K], where K is the class number of the OM sets.

Further, in Avizo, slices are filtered by the non-local means method. Slices are aligned with the Align Slices command. The 3D models are cut to form 1 μm*1 μm*1 μm cubes. 3D pores are extracted by the threshold segmentation method. The Material Statistics command is used to count the total volume of pores $V_{Tm}$, and the Connected Components command is used to calculate the volume $V_{Cm}$ of connected pores, and calculate the proportion of connected pores (that is, the pore connectivity parameter). In this example, for the class I OM, the volume $V_{CI}$ of connected pores is 0.46 μm³, the total volume $V_{TI}$ of pores is 0.48 μm³, and the pore connectivity parameter $P_1$ is 0.98. For the class II OM, the volume $V_{CII}$ of connected pores is 0.05 μm³, the total volume $V_{TII}$ of pores is 0.08 μm³, and the proportion $P_{II}$ of connected pores is 0.58. For the class III OM, the volume $V_{CIII}$ of connected pores is 0.12 μm³, the total volume $D_{TIII}$ of pores is 0.31 μm³, and the proportion $P_{III}$ of connected pores is 0.39. The class IV OM has very few connected pores and can be approximately considered as disconnected.

S600: Acquire an evaluation index for overall connectivity of the OM-hosted pores in the shale based on the pore connectivity parameter.

The evaluation index for the overall connectivity is $C_r$, $$C_r = \frac{\left\{\sum_{m}^{k}(P_m * \emptyset_m)\right\}}{\emptyset_{total}} * 100\%,$$

100%, where $\emptyset_m$ is a total plane porosity of the m-th class of OM set; and $\emptyset_{total}$ is a total plane porosity of the K classes of OM sets in the shale sample.

$\emptyset_m = \Sigma\emptyset_o$, where $\emptyset_o$ is a plane porosity of an o-th OM in each class of OM set, o∈[1, N].

$\emptyset_o = S_{po}/S*100\%$.

$S_{po} = \Sigma A_{pi}$, where $S_{po}$ is an area of all pores in the o-th OM in each class of OM set.

$\emptyset_{total} = \Sigma\emptyset_m$.

$$C_r = \frac{\left\{\sum_{m}^{k}(P_m * \emptyset_m)\right\}}{\emptyset_{total}} * 100\%.$$

In this example, the total plane porosity $\emptyset_I$ of the class I OM is 1.07%, the total plane porosity $\emptyset_{II}$ of the class II OM is 0.49%, the total plane porosity $\emptyset_{III}$ of the class III OM is 0.31%, the total plane porosity $\emptyset_{IV}$ of the class IV OM is 0.01%, and the total plane porosity $\Phi_{Total}$ of all OM sets in the shale sample is: 1.07%+0.49%+0.31%+0.01%=1.88%.

$$C_r = \frac{P_I * \emptyset_I + P_{II} * \emptyset_{II} + P_{III} * \emptyset_{III} + P_{IV} * \emptyset_{IV}}{\emptyset_{total}} * 100\%.$$

$$C_r = \frac{0.98 * 1.07\% + 0.58 * 049\% + 0.39 * 0.31\% + 0 * 0.01\%}{1.88\%} * 100\% = 77.32\%.$$

In the present invention, the overall connectivity of the OM-hosted pores in the tested shale sample is quantitatively evaluated according to $C_r$, and a greater $C_r$ indicates a higher connectivity of the OM-hosted pores in the sample.

Although the present invention has been described with reference to the preferred examples, various improvements can be made and components therein can be replaced with equivalents without departing from the scope of the present invention. In particular, as long as there is no structural conflict, the technical features in the examples can be combined in any way. The present invention is not limited to the specific examples disclosed herein, but shall include all technical solutions falling within the scope of the claims.

In the description of the present invention, terms such as "central", "upper", "lower", "left", "right", "vertical", "horizontal", "inner", and "outer" indicate orientation or position relationships based on the accompanying drawings. They are merely intended to facilitate description, rather than to indicate or imply that the mentioned apparatus or components must have the specific orientation and must be constructed and operated in the specific orientation. Therefore, these terms should not be construed as a limitation to the present invention. Moreover, the terms such as "first", "second", and "third" are used only for description and are not intended to indicate or imply relative importance.

It should be noted that in the description of the present invention, unless otherwise clearly specified, meanings of terms "install", "connect with" and "connect to" should be understood in a broad sense. For example, the connection may be a fixed connection, a removable connection, or an integral connection; may be a mechanical connection or an electrical connection; may be a direct connection or an indirect connection via a medium; or may be an internal connection between two assemblies. Those skilled in the art should understand the specific meanings of the above terms in the present invention based on specific situations.

In addition, terms "include", "comprise", or any other variations thereof are intended to cover non-exclusive inclusions, so that a process, an article, or a device/apparatus including a series of elements not only includes those elements, but also includes other elements that are not explicitly listed, or also includes inherent elements of the process, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions derived by making these changes or substitutions should fall within the protection scope of the present invention.

What is claimed is:

1. A classified characterization method for connectivity of organic matter (OM)-hosted pores in shale, comprising the following steps:
   S100: scanning a shale sample according to a preset imaging area through a scanning electron microscope to acquire a two-dimensional (2D) image of the shale sample;
   S200: extracting pore parameters of each OM in the 2D image by Avizo software, wherein the pore parameters comprise porosity $\varphi_{OM}$, median pore radius Md, pore sorting coefficient $S_o$, and pore shape factor SF of the OM;
   S300: acquiring a class number of OM sets according to the pore parameters, wherein step S300 comprises:
     S310: performing an initial classification on the OM sets through a K-means clustering algorithm based on the porosity, the median pore radius, the pore sorting coefficient and the pore shape factor, wherein an initial class number of the OM sets is K, K≥2, and each of the OM sets comprises N OM, wherein N is a natural number greater than 1;
     S320: calculating a coefficient of variation $CV_j$ of each class of OM sets through the K-means clustering algorithm, $CV_j = \sigma_j/\mu_j$, wherein j is $\varphi_{OM}$, Md, $S_o$ or SF; $\sigma_j$ is a standard deviation (SD) of corresponding j of the N OM in each class of OM sets; and $\mu_j$ is a mean of the corresponding j of the N OM in each class of OM sets; and
     S330: when any coefficient of variation $CV_j$ in the K classes of OM sets satisfies $CV_j \leq 0.5$, taking the initial class number K of the OM sets as the class number of the OM sets; and otherwise, proceeding to S340; and
     S340: setting the initial class number of the OM sets to K=K+1, and repeating S320 to S330;
   S400: performing three-dimensional (3D) reconstruction on each class of OM sets through a focused ion beam-helium ion microscope to acquire reconstructed 3D models of the OM;
   S500: acquiring a pore connectivity parameter based on the reconstructed 3D models of the OM by the Avizo software, wherein the pore connectivity parameter is $P_m$, $P_m = V_{Cm}/V_{Tm}$; $P_m$ is a pore connectivity parameter of an m-th class of OM set, $V_{Cm}$ is a volume of connected pores in the m-th class of OM set, and $V_{Tm}$ is a volume of total pores in the m-th class of OM set; m∈[1, K], wherein K is the class number of the OM sets; and
   S600: acquiring an evaluation index for overall connectivity of the OM-hosted pores in the shale based on the pore connectivity parameter.

2. The classified characterization method according to claim 1, wherein
   a method for acquiring the 2D image comprises:
   S110: performing argon ion polishing on the shale sample to acquire a pretreated shale sample;
   S120: setting an acceleration voltage of the scanning electron microscope to 1.2 kV, and acquiring a secondary electron signal on a surface of the pretreated shale sample at a preset imaging resolution; and
   S130: performing, by the scanning electron microscope, continuous 2D splicing imaging on the pretreated shale sample according to the preset imaging area, wherein the preset imaging area is S, and S>100 μm*100 μm.

3. The classified characterization method according to claim 2, wherein
   the preset imaging resolution is 4 nm/pixel; and
   the preset imaging area is 260 μm*260 μm.

4. The classified characterization method according to claim 2, wherein
   a method for extracting the pore parameters comprises:
   S210: preprocessing the 2D image to acquire a preprocessed image, wherein the preprocessing comprises grayscale correction and filtering;
   S220: extracting all OM in the preprocessed image by threshold segmentation based on a grayscale difference, and storing the extracted all OM in a binarized form to acquire a binarized image;
   S230: acquiring a first OM region image based on the binarized image, wherein the first OM region image comprises N first OM regions, and each of the N first OM regions has a closed-loop structure composed of a same grayscale;
   S240: assimilating different grayscales in the N first OM regions through a filling command to acquire a filled second OM region image, wherein the filled second OM region image comprises N second OM regions, and the N second OM regions correspond to the N first OM regions, respectively;
   S250: sequentially assigning values to the N second OM regions through MATLAB software to acquire a third OM region image with different assigned regions, wherein the third OM region image comprises N third OM regions, and assignment numbers of the N third OM regions are defined by a first set of Arabic numerals in a first order;
   S260: sequentially assigning values to the N first OM regions through the MATLAB software to acquire a fourth OM region image with different assigned regions, wherein the fourth OM region image comprises N fourth OM regions, and assignment numbers of the N fourth OM regions are defined by a second set of Arabic numerals in a second order; and the second order is set in accordance with the first order, and the first set of Arabic numerals is set in accordance with the second set of Arabic numerals;
   S270: subtracting the third OM region image from the fourth OM region image to acquire a fifth OM region image, wherein the fifth OM region image comprises N fifth OM regions, and the N fifth OM regions are labeled pore images, wherein values are assigned to the labeled pore images sequentially; and
   S280: acquiring the porosity $\varphi_{OM}$, the median pore radius Md, the pore sorting coefficient $S_o$ and the pore shape factor SF based on the fifth OM region image;
   wherein, $\varphi_{OM} = A_p/(A_{QM}+A_p)*100\%$, $A_{OM}$ is an area of a single OM, and $A_p$ is an area of pores in the single OM;
   the median pore radius Md is a pore radius corresponding to 50% on a cumulative pore size distribution curve, wherein the cumulative pore size distribution curve is a distribution curve of a pore radius and a cumulative percentage of a pore area; and
   $S_o = P_{25}/P_{75}$, wherein, $P_{25}$ and $P_{75}$ respectively represent pore radii corresponding to cumulative percentages 25% and 75% of the pore area on the cumulative pore size distribution curve;
   calculating N pore shape factors $SF_i$ corresponding to the N fifth OM regions, $SF_i = 4\pi A_{pi}/L_{pi}^2$, wherein $SF_i$ is a pore shape factor of an i-th pore, $A_{pi}$ is an area of the i-th pore, and $L_{pi}$ is a perimeter of the i-th pore, i∈[1, N];

selecting pore shape factors with a same value to form a set of identical factors, wherein the N pore shape factors form M sets of identical factors, and M∈(1, N);

wherein, each of the sets of identical factors comprises n pore shape factors, n∈(1, N);

acquiring a sum of areas of pores corresponding to each set of identical factors to form a set of pore areas, wherein the M sets of identical factors form M sets of pore areas; and acquiring, based on the M sets of pore areas, a pore shape factor corresponding to a set of pore areas with a maximum sum of areas to be the pore shape factor SF.

5. The classified characterization method according to claim 4, wherein $$\sigma_{\varphi_{OM}} = \sqrt{\frac{\sum_{i=1}^{N}(\varphi_{OM,i} - \mu_{\varphi_{OM}})^2}{N}},$$

wherein $\sigma_{\varphi OM}$ is standard deviation, (SD) of porosities corresponding to the N OM in each class of OM sets;

$$\mu_{\varphi_{OM}} = \frac{\sum_{i=1}^{N}\varphi_{OM,i}}{N},$$

wherein $\mu_{\varphi OM}$ is a mean of porosities corresponding to the N OM in each class of OM sets;

$$\sigma_{Md} = \sqrt{\frac{\sum_{i=1}^{N}(Md_i - \mu_{Md})^2}{N}},$$

wherein $\sigma_{Md}$ is an SD of median pore radii corresponding to the N OM in each class of OM sets;

$$\mu_{Md} = \frac{\sum_{i=1}^{N} Md_i}{N},$$

wherein $\mu_{Md}$ is a mean of median pore radii corresponding to the N OM in each class of OM sets;

$$\sigma_{S_o} = \sqrt{\frac{\sum_{i=1}^{N}(S_{o,i} - \mu_{S_o})^2}{N}},$$

wherein $\sigma_{S_o}$ is an SD of pore sorting coefficients corresponding to the N OM in each class of OM sets;

$$\mu_{S_o} = \frac{\sum_{i=1}^{N} S_{o,i}}{N},$$

wherein $\mu_{S_o}$ is a mean of pore sorting coefficients corresponding to the N OM in each class of OM sets;

$$\sigma_{SF} = \sqrt{\frac{\sum_{i=1}^{N}(SF_i - \mu_{SF})^2}{N}},$$

wherein $\sigma_{SF}$ is an SD of pore shape factors corresponding to the N OM in each class of OM sets; and $$\mu_{SF} = \frac{\sum_{i=1}^{N} SF_i}{N},$$

wherein $\mu_{SF}$ is a mean of pore shape factors corresponding to the N OM in each class of OM sets.

6. The classified characterization method according to claim 5, wherein
a method for acquiring the reconstructed 3D models of the OM comprises: screening the K classes of OM sets based on a preset area threshold by the focused ion beam-helium ion microscope to acquire the reconstructed 3D models of the OM, wherein the preset area threshold is S1, S1>5 μm*5 μm.

7. The classified characterization method according to claim 6, wherein
the evaluation index for the overall connectivity is $C_r$, $$C_r = \frac{\left\{\sum_{m}^{k}(P_m * \varnothing_m)\right\}}{\varnothing_{total}} * 100\%,$$

wherein $\varnothing_m$ is a total plane porosity of the m-th class of OM set, and $\varnothing_{total}$ is a total plane porosity of the K classes of OM sets in the shale sample;

$\varnothing_m = \Sigma\varnothing_o$, wherein $\varnothing_o$ is a plane porosity of an o-th OM in each class of OM sets, o∈[1, N];

$\varnothing_o = S_{po}/S*100\%$;

$S_{po} = A_{pi}$, wherein $S_{po}$ is an area of all pores in the o-th OM in each class of OM sets; and $\varnothing_{total} = \Sigma\varnothing_m$.

8. The classified characterization method according to claim 4, wherein SF∈(0,1].

* * * * *